United States Patent [19]

Hirao

[11] 3,940,325
[45] Feb. 24, 1976

[54] RADIATION-STERILIZED SHAPED ARTICLES OF OLEFIN POLYMERS
[75] Inventor: Seiji Hirao, Ichihara, Japan
[73] Assignee: Chisso Corporation, Osaka, Japan
[22] Filed: Aug. 24, 1973
[21] Appl. No.: 391,413

[30] Foreign Application Priority Data
Aug. 24, 1972 Japan.............................. 47-84715

[52] U.S. Cl. 204/159.20; 204/159.17; 260/45.85 E; 260/23 H; 21/2
[51] Int. Cl......... B01j 1/10; C08f 45/58; C08f 1/10
[58] Field of Search................. 204/159.17, 159.20; 260/45.85 B; 21/2

[56] References Cited
UNITED STATES PATENTS
2,997,454  8/1961  Liistner et al................ 260/45.85 E
3,280,069  10/1966  Knapp et al. ................ 260/45.85 V
3,313,771  4/1967  Dressler et al. .............. 260/45.85 E
3,537,967  11/1970  Kelly et al..................... 204/159.18
3,714,122  1/1973  Kline............................ 260/45.85 B Primary Examiner—John C. Bleutge
Assistant Examiner—Thurman Kennis Page
Attorney, Agent, or Firm—Fred Philpitt

[57] ABSTRACT

Radiation-sterilized shaped articles of olefin polymers containing 0.01 – 0.5% by weight based on the weight of the olefin polymers, of octadecyl 3,5-di-t-butyl-4-hydroxyhydrocinnamate or/and tetrakis [methane (3,5-di-t-butyl-4-hydroxyhydrocinnamate)] methane. The radiation-sterilized shaped articles are colorless and still have practically acceptable physical properties (melt flow rate and percentage occurrence of cracking), in spite of the fact that they have been irradiated with high energy radiation.

6 Claims, No Drawings

RADIATION-STERILIZED SHAPED ARTICLES OF OLEFIN POLYMERS

DESCRIPTION OF THE INVENTION

This invention relates to shaped articles of olefin polymers irradiated with radiant rays. More particularly, it relates to shaped articles of olefin polymers which have been sterilized by means of γ-ray-irradiation without accompaniment of discoloration and degradation in physical properties due to said irradiation.

Olefin polymers usually contain various kinds of stabilizers and additives depending upon the application fields and objects in order to maintain and develop their useful properties. For polyolefins (particularly polypropylene and polyethylene), there are a great variety of application fields now but they have recently found utility also in medical instruments and food-packagings. It goes without saying that shaped articles to be used for medical treatments and food-packagings must undergo the treatment of sterilization or disinfection, and this is a point of this application different from usual application. For sterization purpose, it is now recognized that irradiation of a dose of 2.5–6 megarads of γ-ray is very effective. However, it has heretofore been a well known fact that usual polyolefins, when treated with a high dose of radiation energy, always exhibit remarkable coloration. It is presumed that such coloration is caused mainly by additives, since no coloration is observed when γ-ray is irradiated on polymers which do not contain any additive such as stabilizer. The polymers which do not contain additive, nevertheless, exhibit remarkable degradation in physical properties after irradiation of γ-ray, and hence cannot be used for producing shaped articles. Thus, adevent of polymers which do not show coloration nor degradation in physical properties even when irradiated with γ-ray has been desired.

Canadian patent No. 811,766 discloses an improvement of method for preventing polymers from being colored during the time of irradiation with high energy radiant ray, which comprises adding thiodipropionic acid diesters including distearyl thiodipropionate to crystalline propylene polymers. However, the addition of such compounds may prevent coloration due to irradiation of γ-ray, but cannot prevent degradation in physical properties. Polymers containing distearyl thiodipropionate alone are almost similar in physical properties to those having no stabilizer.

The object of the present invention is accordingly to provide shaped articles of olefin polymers irradiated with γ-ray without accompaniment of coloration or degradation in physical properties during the irradiation. The object and other advantages can be attained by the present invention mentioned below.

The present invention resides in shaped articles of olefin polymers obtained by shaping an olefin polymer or polymers containing 0.01–0.5% by weight based on the weight of the olefin polymers, of octadecyl 3,5-di-t-butyl-4-hydroxyhydrocinnamate or/and tetrakis [methylene (3,5-di-t-butyl-4-hydroxyhydrocinnamate)] methane, and then subjecting the resulting shaped article to a sterilizing dose of high energy radiation.

As for the above-mentioned olefin polymers, there can be illustrated homopolymers of propylene; homopolymers of propylene containing therein 0.1–4% by weight based on the weight of homopolymers of propylene, of ethylene-propylene rubber (EPR); propylene-ethylene copolymers containing 0.5–20% by weight based on the weight of propylene, of ethylene; high density polyethylenes having a density of 0.950 to 0.965 g/c.c.; low density polyethylenes having a density of 0.905 to 0.925 g/c.c.; homopolymers of propylene containing therein 0.5–4% by weight based on the weight of homopolymers of propylene, of high density or low density polyethylene; or the like.

As for the above-mentioned shaped articles of the present invention, there can be illustrated instruments for medical treatment such as syringes, forceps, surgical clamps, etc., bags for food packaging, vessels for food packaging, etc. They are produced by various kinds of conventional molding processes such as injection molding, compression molding, extrusion molding, vacuum molding, etc.

Addition of 0.01–0.3% by weight based on the weight of olefin polymers, metal salts of fatty acids (mainly calcium stearate) to the above-mentioned olefin polymers in addition to the above-mentioned compounds, octadecyl 3,5-di-t-butyl-4-hydroxyhydrocinnamate or-/and tetrakis [methylene(3,5-di-t-butyl-4-hydroxyhydrocinnamate)] methane, does not cause any coloration nor has bad influence upon the effectiveness of the above-mentioned cinnamates.

Further, for utilities which require slipping property such as syringes or the like, 0.01–0.5% by weight based on the weight of olefin polymers, of fatty acid amides may be further added.

Furthermore, in order to increase the effectiveness for preventing degradation in physical properties, 0.01–0.5% by weight based on the weight of olefin polymers, of at least one of dilauryl thiodipropionate, distearyl thiodipropionate and distearyl thiodibutyrate, can be added, and in this case, better results can be obtained due to synergism.

The high energy radiation useful for sterilization purposes is conveniently provided by a cobalt 60 source. Other sterilizing radiation treatment, however, can be used, such as high energy X-rays, so long as the sterilization is accomplished by this treatment. The dosage applied to the polymers should be sufficient only to sterilize the composition. For the olefin polymers of this invention, a shaped article such as a syringe can be effectively sterilized by applying 2.5 megarads.

In general, radiation dosages that can be applied range from about 2.5 to about 6 megarads.

The mixing ratio of additives referred to herein is based upon the weight of olefin polymers unless otherwise indicated.

The present invention is further illustrated by the following examples, but they should not be construed to be limitative to the scope of the present invention.

EXAMPLES

Olefin polymers were shaped into 20 ml syringe by means of an injection molding machine, and the resulting syringe was subjected to irradiation of γ-ray of 5 megarads (ray source: cobalt 60).

In the following Table are shown kinds of olefin polymers, kinds and amounts of additives, MFR (1) (according to ASTM D-1238) prior to γ-ray irradiation, and MFR (2), color and percentage occurrence of cracking after γ-ray irradiation. The percentage occurrence of cracking referred to herein means the ratio of the number of cracked syringes to five of same syringes.

Table

| Sample No. | Polymer | Additive | % | MFR (1) | After irradiation Color | MFR (2) | Occurrence of cracking, % |
|---|---|---|---|---|---|---|---|
| 1 | PP | None | | 11.0 | colorless | 300 or more | 100 |
| 2 | PP | Ca-St | 0.1 | 10.5 | colorless | 300 or more | 100 |
| 3 | PP | BHT<br>Ca-St | 0.1<br>0.1 | 5.1 | light yellow | 50 | 40 |
| 4 | PP | S.W.P<br>Ca-St | 0.1<br>0.1 | 5.7 | light yelow | 43 | 40 |
| 5 | PP | Irganox 565<br>Ca-St | 0.1<br>0.1 | 5.8 | light yellow | 48 | 40 |
| 6* | PP | Irganox 1076<br>Ca-St | 0.1<br>0.1 | 6.7 | colorless | 51 | 40 |
| 7* | PP | Irganox 1010<br>Ca-St | 0.1<br>0.1 | 6.9 | colorless | 48 | 40 |
| 8 | PP | Topanol CA<br>Ca-St | 0.1<br>0.1 | 7.4 | yellow | 59 | 40 |
| 9 | PP | Ionox 330<br>Ca-St | 0.1<br>0.1 | 5.7 | light yellow | 50 | 40 |
| 10 | PP | GRA<br>Ca-St | 0.1<br>0.1 | 5.8 | light yellow | 52 | 40 |
| 11 | PP | GRB<br>Ca-St | 0.1<br>0.1 | 6.2 | light yellow | 53 | 40 |
| 12 | PP | Santonox R<br>Ca-St | 0.1<br>0.1 | 5.1 | brown | 86 | 60 |
| 13 | PP | DLTDP<br>Ca-St | 0.1<br>0.1 | 7.0 | colorless | 94 | 80 |
| 14 | PP | DSTDP<br>Ca-St | 0.1<br>0.1 | 6.8 | colorless | 90 | 80 |
| 15 | PP | DSTDB<br>Ca-St<br>BHT | 0.1<br>0.1<br>0.1 | 6.8 | colorless | 96 | 80 |
| 16 | PP | DLTDP<br>Ca-St<br>S.W.P. | 0.2<br>0.1<br>0.1 | 5.0 | yellowish brown | 44 | 60 |
| 17 | PP | DSTDP<br>Ca-St<br>Irganox 1076 | 0.2<br>0.1<br>0.1 | 5.2 | yellow | 43 | 40 |
| 18* | PP | DLTDP<br>Ca-St<br>Irganox 1010 | 0.2<br>0.1<br>0.1 | 6.0 | colorless | 47 | 20 |
| 19* | PP | DSTDP<br>Ca-St<br>Ionox 330 | 0.2<br>0.1<br>0.1 | 6.1 | colorless | 45 | 20 |
| 20 | PP | DLTDP<br>Ca-St | 0.2<br>0.1 | 5.6 | yellow | 51 | 40 |
| 21 | PP | Amide-A<br>Ca-St | 0.3<br>0.1 | 9.6 | colorless | 300 or more | 100 |
| 22 | PP | Amide B<br>Ca-St<br>Irganox 1076 | 0.3<br>0.1<br>0.1 | 9.9 | colorless | 300 or more | 100 |
| 23* | PP | DLTDP<br>Amide-A<br>Ca-St<br>Irganox 1010 | 0.2<br>0.3<br>0.1<br>0.1 | 6.0 | colorless | 48 | 20 |
| 24* | PP | DLTDP<br>Amide-B<br>Ca-St<br>Irganox 1010 | 0.2<br>0.3<br>0.1<br>0.1 | 5.8 | colorless | 44 | 20 |
| 25* | P-E Copoly.<br>($C_2^=$ = 1.0%) | DLTDP<br>Ca-St<br>Irganox 1076 | 0.2<br>0.1<br>0.1 | 6.4 | colorless | 40 | 0 |
| 26* | PP + EPR3% | DLTDP<br>Ca-St<br>Irganox 1010 | 0.2<br>0.1<br>0.1 | 6.2 | colorless | 45 | 0 |
| 27* | LDPE | DLTDP<br>Ca-St<br>Irganox 1010 | 0.2<br>0.1<br>0.1 | 5.0** | colorless | 4.7 ** | 0 |
| 28* | HDPE | Ca-St<br>DLTDP | 0.1<br>0.2 | 5.0** | colorless | 4.8 ** | 0 |
| 29* | PP + LDPE3% | Irganox 1010<br>Ca-St | 0.1<br>0.1 | 7.0 | colorless | 38 | 0 |
| 30* | PP + HDPE3% | Irganox 1076 | 0.1 | 6.5 | colorless | 32 | 0 |

Table-continued

| Sample No. | Polymer | Additive | % | MFR (1) | After irradiation Color | MFR (2) | Occurrence of cracking, % |
|---|---|---|---|---|---|---|---|
| | | Ca-St | 0.1 | | | | |

Notes:
PP : Polypropylene
P-E Copoly. : Propylene ethylene copolymer
$C_2^=$ : Ethylene content
LDPE : Low density polyethylene
HDPE : High density polyethylene
Ca-St : Calcium stearate
BHT : 2,6-di-t-butyl-p-cresol
S.W.P : 4,4-butylidene bis (6-t-butyl-m-cresol)
Irganox 565 : 2,4 bis-(n-octylthio)-6-(4-hydroxy-3,5-di-t-butylanilino)-1,3,5 triazine
Irganox 1076 : Octadecyl 3,5-di-t-butyl-4-hydroxyhydrocinnamate
Irganox 1010 : Tetrakis [methylene (3,5-di-t-butyl-4-hydroxyhydrocinnamate)] methane
Topanol CA : 1,1,3 tris (2-methyl-5-t-butyl-4-hydroxyphenol) butane
Ionox 330 : 1,3,5 trimethyl 2,4,6 tris (3,5-di-t-butyl-4-hydroxybenzyl) benzene
GRA : Tris (3,5-di-t-butyl-4-hydroxybenzyl) isocyanurate
GRB : Tris [β(4-hydroxy-3,5-di-t-butylphenyl) propionyloxyethyl] isocyanurate
Santonox R : 4,4' thio bis (2-t-butyl-5-methylphenol)
DLTDP : Dilauryl β,β'-thiodipropionate
DSTDP : Distearyl β,β'-thiodipropionate
DSTDB : Distearyl β,β'-thiobutyrate
Amide A : Oleic amide
Amide B : Erucic amide
* : Examples according to the present invention
** : M.I. (according to ASTMD-1238)

As apparent from the above Table, the shaped articles of the compositions having therein distearyl thiodipropionate incorporated (sample Nos. 13, 14 and 15) have no commercial value as products in view of their poor physical properties (MFR (2) and percentage occurrence of cracking). On the other hand, the shaped articles of the present invention (sample Nos. 6,7,18,19,23,24,25,26,27, 28,29 and 30) are exceedingly superior to those of the above-mentioned prior art (Canadian patent) using thiodipropionic acid diesters.

What is claimed is:

1. Shaped articles comprising at least one polymer selected from the group consisting of homopolymers of propylene; homopolymers of propylene containing therein 0.1–4% by weight based on the weight of homopolymers of propylene, of ethylene-propylene rubber; propylene-ethylene copolymers containing therein 0.5–20% by weight based on the weight of propylene, of ethylene; high density polyethylenes having a density of 0.950 to 0.965 g/cc.; g/cc.; low density polyethylenes having a density of 0.905 to 0.925 g/c.c.; and homopolymers of propylene containing therein 0.5–4% by weight based on the weight of homopolymers of propylene, of high density or low density polyethylene and 0.01–0.5% by weight based on the weight of the olefin polymer or polymers, of at least one material selected from the group consisting of octadecyl 3,5-di-t-butyl-4-hydroxyhydrocinnamate and tetrakis (methylene(3,5-di-t-butyl -4-hydroxyhydrocinnamate)) methane, and irradiated with a sterilizing dose of high energy radiation.

2. Shaped articles according to claim 1, wherein said olefin polymer or polymers further contain 0.01 to 0.3% by weight based on the weight of the olefin polymer or polymers, of calcium stearate.

3. Shaped articles according to claim 1 wherein said olefin polymer or polymers further contain 0.01 to 0.3% by weight of calcium stearate and 0.01 to 0.5% by weight of at least one material selected from the group consisting of oleic amide and erucic amide, both based on the weight of the olefin polymer or polymers.

4. Shaped articles according to claim 1, wherein said olefin polymer or polymers further contain 0.01 to 0.3% by weight of calcium stearate and 0.01 to 0.5% by weight of at least one compound selected from the group consisting of dilauryl thiodipropionate, distearyl thiodipropionate and distearyl thiodibutyrate, both based on the weight of the olefin polymer or polymers.

5. Shaped articles according to claim 1, wherein said olefin polymer or polymers further contain 0.01 to 0.3% by weight of calcium stearate, 0.01 to 0.5% by weight of at least one material selected from the group consisting of oleic amide and erucic amide and 0.01 to 0.5% by weight of at least one material selected from the group consisting of dilauryl thiodipropionate, distearyl thiodipropionate and distearyl thiodibutyrate, each based on the weight of the olefin polymer or polymers.

6. A process for producing radiation-sterilized shaped articles of an olefin polymer without coloration and degradation in physical properties, which comprises shaping an olefin polymer or polymers containing 0.01 to 0.5% by weight based on the weight of the olefin polymer of at least one material selected from the group consisting of octadecyl 3,5-di-t-butyl-4-hydroxyhydrocinnamate and tetrakis (methylene (3,5-di-t-butyl-4hydroxyhydrocinnamate)) methane, and then irradiating with a sterilizing dose of high energy radiation, said olefin polymer being selected from the group consisting of homopolymers of propylene; homopolymers of porpylene containing therein 0.1–4% by weight based on the weight of homopolymers of propylene, of ethylene-propylene rubber; propylene-ethylene copolymers containing therein 0.5–20% by weight based on the weight of propylene, of ethylene; high density polyethylenes having a density of 0.950 to 0.965 g/c.c.; low density polyethylenes having a density of 0.905 to 0.925 g/c.c.; and homopolymers of propylene containing therein 0.5–4% by weight based on the weight of homopolymers of propylene, of high density or low density polyethylene.

* * * * *